(12) United States Patent
Reilly, III

(10) Patent No.: US 11,980,608 B1
(45) Date of Patent: May 14, 2024

(54) TREATMENT OF PROTEOGLYCAN ACCUMULATION DISEASES

(71) Applicant: Frank Kelly Reilly, III, West Chester, PA (US)

(72) Inventor: Frank Kelly Reilly, III, West Chester, PA (US)

( * ) Notice: Subject to any disclaimer, the term of this patent is extended or adjusted under 35 U.S.C. 154(b) by 0 days.

(21) Appl. No.: 18/131,896

(22) Filed: Apr. 7, 2023

(51) Int. Cl.
*A61K 31/415* (2006.01)
*A61K 31/365* (2006.01)
*A61K 45/06* (2006.01)

(52) U.S. Cl.
CPC .......... *A61K 31/415* (2013.01); *A61K 31/365* (2013.01); *A61K 45/06* (2013.01)

(58) Field of Classification Search
CPC ........................... A61K 31/415; A61K 31/365
USPC ......................................................... 514/406
See application file for complete search history.

(56) References Cited

U.S. PATENT DOCUMENTS 9,982,288 B2 * 5/2018 Shimada .................. C12Q 1/44
2019/0076376 A1 * 3/2019 Brothers ................ A61K 31/69

* cited by examiner

*Primary Examiner* — Raymond J Henley, III
(74) *Attorney, Agent, or Firm* — Joseph E. Maenner; Petock & Petock LLC

(57) ABSTRACT

A method for controlling proteoglycan accumulation disease includes the use of a pharmaceutically efficient amount of a COX2 inhibitor NSAID.

26 Claims, No Drawings

TREATMENT OF PROTEOGLYCAN ACCUMULATION DISEASES

BACKGROUND OF THE INVENTION

Field of the Invention

The invention relates to pharmaceuticals and methods for treating proteoglycan accumulation diseases in humans and all animals.

Description of the Related Art

Proteoglycan accumulation disease is a rare genetic disorder in which abnormal amounts of proteoglycans accumulate in different parts of the body. It is characterized by progressive stiffness and deformity of the joints and abnormal thickening of certain tissues. The accumulation of proteoglycans can also lead to serious complications, such as respiratory failure and heart failure.

It would be beneficial to provide an effective pharmaceutical and method of treatment of proteoglycan accumulation diseases.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a method for controlling proteoglycan accumulation disease comprising a use of a pharmaceutically efficient amount of a COX2 inhibitor NSAID.

DETAILED DESCRIPTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present invention provides a method for controlling proteoglycan accumulation disease, including the prevention and treatment of such disease. The method comprising a use of a pharmaceutically efficient amount of a selective COX2 inhibitor NSAID pharmaceutical for the control of proteoglycan accumulation diseases, including abnormal glycosaminoglycan component of proteoglycan in animals and humans, including proteoglycan accumulation in increased size of cells or in the increased number of cells to create disease or create complications of other diseases, and includes genetic causes and acquired causes of accumulation or abnormality.

The COX2 inhibitor NSAID covers all forms, isomers, and salts of COX2 inhibitor NSAIDS, including selective COX2 inhibitors, and can be administered by at least one of orally, topically, intravenously, intramuscularly, injectably, and by coating of any body structures.

An exemplary COX2 inhibitor NSAID comprises firocoxib for use in animals, including, but not limited to dogs and horses. In an alternative embodiment, the COX2 NSAID inhibitor comprises celecoxib for use in humans. The cox2 NSAID inhibitor used in the present treatment method can be used in combination with other medications, vitamins, herbal remedies, and/or therapeutics. the other therapeutics comprise at least one from the list of antibiotics, immunoglobulins, immune therapy, anti-cancer medications or treatments, antihistamines, other nsaids that are not selective cox2 inhibitors, calcium channel blockers (exemplary calcium channel blocker comprising amlodipine) hormones including levothyroxine and de-wormers (exemplary diethylcarbamazine), and aspirin in all of its forms including, but not limited to the soluble lysine salt of aspirin in all of its modes of administration including but not limited to oral, topical, injectable, and inhalable.

Exemplary proteoglycan accumulation diseases that can be treated by the present method include, but are not limited to ehlers danlos in animals and/or humans, including but not limited to multiple forms of this disease to cover all of them including ligament/tendon/internal organs/eyes; in animals, degenerative suspensory ligament disease (dsld), is an example and is part of ehlers danlos in animals; ovarian cancer in humans; alzheimer's disease, including but not limited to plaque including omxloid+Tau, and other proteoglycans yet to be delineated; Multiple Sclerosis in any of its multiple forms; Eczema; Psoriasis; Neurological disease of proteoglycan accumulation including psychological diseases including but not limited to bi-polar disorder; Kidney and/or liver defects; Chondrodysplasia; Skeletal exortoris including but not limited to cartilage capped tumors; Granulomatous diseases including but not limited to skin and/or lung diseases; Non-granulomatous lung disease; and lung disorders, including at least one of lung sarcoidosis, extrinsic allergic alveolitis, and tuberculosis.

Alternatively, instead of COX2 inhibitors, calcium channel blockers can be used for the treatment of proteoglycan accumulation diseases. By way of example only, such calcium channel blockers can include, among others, dihydropyridines and non-dihydropyridines. Exemplary dihydropyridines can include, among others, Amlodipine and exemplary non-dihydropyridines can include benzothiazepine.

Still alternatively, instead of COX2 or calcium channel blockers, natural or synthetic levothyroxine thyroid hormone can be used for the treatment of proteoglycan accumulation diseases to ensure that blood levels of thyroid hormones remain in a normal-to-high normal range to avoid hypo or hyper thyroid levels.

Yet still alternatively, instead of COX2 or calcium channel blockers, or levothyroxine thyroid hormone, diethylcarbamazine can be used for the treatment of proteoglycan accumulation diseases.

It will be further understood that various changes in the details, materials, and arrangements of the parts which have been described and illustrated in order to explain the nature of this invention may be made by those skilled in the art without departing from the scope of the invention as expressed in the following claims.

I claim:

1. A method for controlling proteoglycan accumulation disease in a patient comprising the step of administering a pharmaceutically efficient amount of a COX2 inhibitor NSAID to the patient.

2. The method according to claim 1, wherein the method comprises treating an abnormal glycosaminoglycan component of proteoglycan.

3. The method according to claim 2, wherein the glycosaminoglycan component comprises proteoglycan linkerpathy.

4. The method according to claim 1, wherein the method comprises treating proteoglycan accumulation in an increased size of cells.

5. The method according to claim 1, wherein the method comprises treating proteoglycan accumulation in an increased number of cells.

6. The method according to claim 1, wherein the COX2 inhibitor NSAID comprises firocoxib for administering to animals.

7. The method according to claim 1, wherein the COX2 NSAID inhibitor comprises celecoxib for administering to humans.

8. The method according to claim 1, wherein the COX2 NSAID inhibitor is administered in combination with other therapeutics.

9. The method according to claim 8, wherein the other therapeutics comprise at least one from the list of antibiotics, immunoglobulins, immune therapy, anticancer medications or treatments, antihistamines, other NSAIDS that are not selective COX2 inhibitors, calcium channel blockers, hormones including levothyroxine and de-wormers, and aspirin in all of its forms comprising the soluble lysine salt of aspirin in all of its modes of administration, comprising at least one of oral, topical, intravenous, injectable, and inhalable.

10. The method according to claim 1, wherein the COX2 inhibitor NSAID is administered by at least one of orally, topically, intravenously, intramuscularly, injectably, and by coating of any body structures.

11. The method according to claim 1, wherein the COX2 inhibitor NSAID comprises isomers and salts of COX2 inhibitor NSAIDS.

12. The method according to claim 1, wherein the proteoglycan accumulation disease comprises a genetically caused proteoglycan accumulation disease.

13. The method according to claim 1, wherein the proteoglycan accumulation disease comprises an acquired proteoglycan accumulation disease.

14. The method according to claim 1, wherein the proteoglycan accumulation disease comprises Ehlers Danlos disease.

15. The method according to claim 1, wherein the proteoglycan accumulation disease comprises ovarian cancer.

16. The method according to claim 1, wherein the proteoglycan accumulation disease comprises Alzheimer's disease.

17. The method according to claim 1, wherein the proteoglycan accumulation disease comprises Multiple Sclerosis.

18. The method according to claim 1, wherein the proteoglycan accumulation disease comprises Eczema.

19. The method according to claim 1, wherein the proteoglycan accumulation disease comprises Psoriasis.

20. The method according to claim 1, wherein the proteoglycan accumulation disease comprises neurological diseases of proteoglycan accumulation, including bi-polar disorder.

21. The method according to claim 1, wherein the proteoglycan accumulation disease comprises at least one of kidney and liver defects.

22. The method according to claim 1, wherein the proteoglycan accumulation disease comprises Chondrodysplasia.

23. The method according to claim 1, wherein the proteoglycan accumulation disease comprises skeletal exortoris.

24. The method according to claim 1, wherein the proteoglycan accumulation disease comprises at least one of skin and lung disease.

25. The method according to claim 1, wherein the proteoglycan accumulation disease comprises non-granulomatorous disease.

26. The method according to claim 1, wherein the proteoglycan accumulation disease comprises lung disorders, comprising at least one of lung sarcoidosis, extrinsic allergic alveolitis, and tuberculosis.

\* \* \* \* \*